(12) United States Patent
Johansen et al.

(10) Patent No.: US 10,495,620 B2
(45) Date of Patent: Dec. 3, 2019

(54) GAS DETECTOR CLOGGING DETECTION

(71) Applicant: SIMTRONICS AS, Oslo (NO)

(72) Inventors: Ib-Rune Johansen, Oslo (NO); Preben Storås, Oslo (NO); Matthieu Lacolle, Nesøya (NO); Dag Thorstein Wang, Oslo (NO); Arne Karlsson, Oslo (NO); Jon Olav Grepstad, Oslo (NO); Michal Marek Mielnik, Jar (NO)

(73) Assignee: Simtronics AS, Oslo (NO)

( * ) Notice: Subject to any disclaimer, the term of this patent is extended or adjusted under 35 U.S.C. 154(b) by 64 days.

(21) Appl. No.: 15/105,447

(22) PCT Filed: Dec. 12, 2014

(86) PCT No.: PCT/EP2014/077502
§ 371 (c)(1),
(2) Date: Jun. 16, 2016

(87) PCT Pub. No.: WO2015/091243
PCT Pub. Date: Jun. 25, 2015

(65) Prior Publication Data
US 2016/0313291 A1    Oct. 27, 2016

(30) Foreign Application Priority Data
Dec. 19, 2013   (NO) .................................. 20131712

(51) Int. Cl.
*G01N 33/00*    (2006.01)
*G01N 21/17*    (2006.01)
(Continued)

(52) U.S. Cl.
CPC ....... *G01N 33/007* (2013.01); *G01N 21/1702* (2013.01); *G01N 21/274* (2013.01);
(Continued)

(58) Field of Classification Search
CPC ............ G01N 33/007; G01N 21/1702; G01N 21/274; G01N 21/645
See application file for complete search history.

(56) References Cited

U.S. PATENT DOCUMENTS

| | | | | |
|---|---|---|---|---|
| 5,218,422 A | * | 6/1993 | Zoechbauer | G01J 3/26 356/454 |
| 5,886,247 A | * | 3/1999 | Rabbett | G01N 21/3504 250/339.13 |

(Continued)

FOREIGN PATENT DOCUMENTS

| | | |
|---|---|---|
| DE | 102010048208 A1 | 4/2012 |
| JP | H02172514 A | 7/1990 |
| JP | 2002081986 A | 3/2002 |

OTHER PUBLICATIONS

English Machine Translation of Ishiwatari et al., JP H02-172514 A, Jul. 4, 1990, Translated Oct. 2017.*

(Continued)

*Primary Examiner* — David Z Huang
(74) *Attorney, Agent, or Firm* — Christopher & Weisberg, P.A.

(57) ABSTRACT

The present invention relates to a gas detector cell unit comprising a gas cell, the unit comprising an outer housing providing access to the gas outside through a protecting filter adapted to making gas cell safe for use in explosive environments, i.e. a sintered filter, and the unit comprising means for detecting reduction in the circulation through said protecting filter.

7 Claims, 4 Drawing Sheets

(51) Int. Cl.
*G01N 21/27* (2006.01)
*G01N 21/64* (2006.01)
*G01N 21/77* (2006.01)

(52) U.S. Cl.
CPC ....... *G01N 21/645* (2013.01); *G01N 33/0006* (2013.01); *G01N 33/0013* (2013.01); *G01N 33/0037* (2013.01); *G01N 33/0044* (2013.01); *G01N 21/643* (2013.01); *G01N 2021/1704* (2013.01); *G01N 2021/7786* (2013.01); *Y02A 50/245* (2018.01)

(56) References Cited

U.S. PATENT DOCUMENTS

| | | | | |
|---|---|---|---|---|
| 6,964,694 | B2* | 11/2005 | Rauchfuss | B01D 46/0086 55/385.3 |
| 7,034,943 | B1* | 4/2006 | Moeckli | G01N 21/1702 250/231.14 |
| 7,178,410 | B2* | 2/2007 | Fraden | A47L 9/19 73/861.52 |
| 7,705,988 | B2* | 4/2010 | Richman | G01J 3/4338 356/432 |
| 2006/0219552 | A1 | 10/2006 | Sasaki et al. | |
| 2007/0013534 | A1 | 1/2007 | DiMaggio | |
| 2007/0285222 | A1* | 12/2007 | Zadnikar | G08B 13/19641 340/509 |
| 2009/0128819 | A1* | 5/2009 | Van Kesteren | A61B 5/083 356/437 |
| 2011/0054811 | A1* | 3/2011 | Contini | B01D 35/143 702/47 |
| 2013/0045541 | A1 | 2/2013 | Fix et al. | |

OTHER PUBLICATIONS

Norwegian Search Report dated Jul. 20, 2014 for Norwegian Patent Application No. 20131712, Filing Date: Dec. 19, 2013 consisting of 2 pages.

International Search Report and Written Opinion dated Jun. 9, 2015 for International Application No. PCT/EP2014/077502, International Filing Date Dec. 12, 2014, consisting of 12 pages.

* cited by examiner

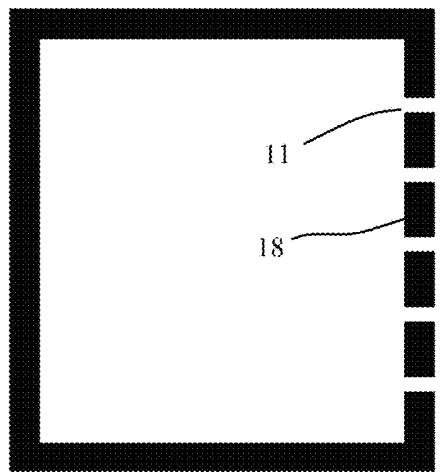
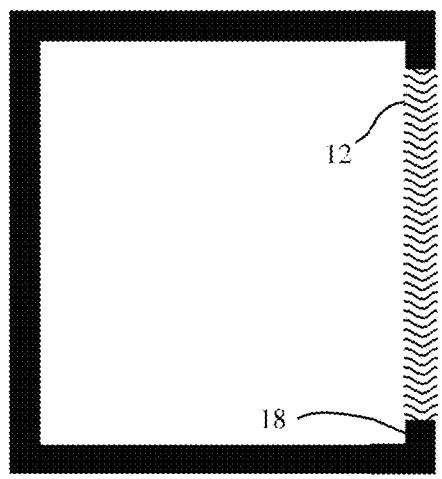
Figure 3a                     Figure 3b
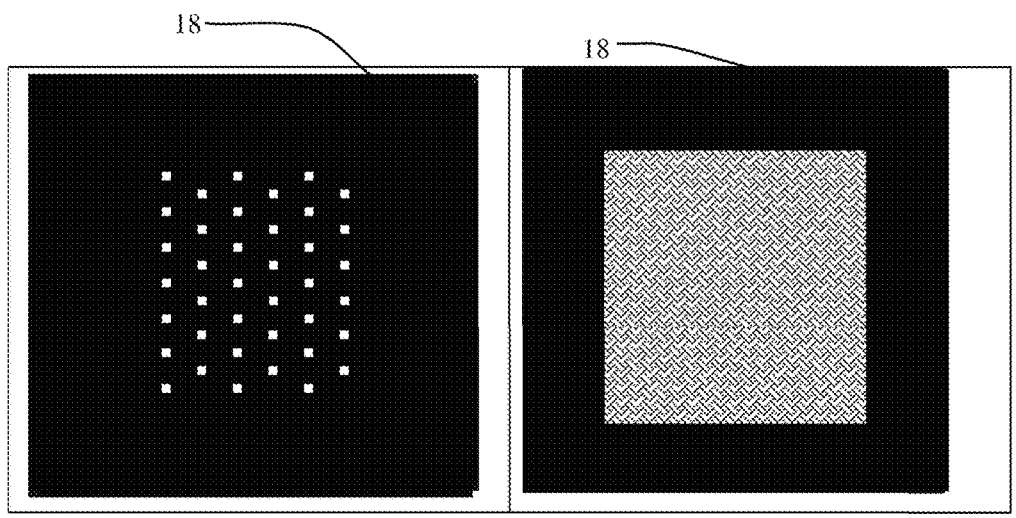
Figure 4a                     Figure 4b

GAS DETECTOR CLOGGING DETECTION

The present invention relates to gas detection, especially related to reliable gas detection in oil and gas installations.

It is a well known problem that poisonous gases may occur in oil production or similar facilities, and optical sensors are commonly used for monitoring such environments by monitoring the absorption spectrum or fluorescence spectrum of a gas, e.g. as described in U.S. Pat. Nos. 5,218,422 and 5,886,247. The measurements are then performed by leading the gas into a measuring cell and transmitting light at a certain wavelength or range of wavelengths through the cell and either directly detecting the absorption on selected, typical wavelengths or measuring the fluorescence spectrum at a detector, often using Fabry-Perot interferometers to select the wavelengths being specific for the gas to be detected. There are, however, some gases that are difficult to detect using optical measuring means as the spectrum coincides with the spectrum of another, often harmless gas. One example of such a gas is $H_2S$ which is difficult to distinguish from water, but is common in oil production and may be very dangerous. $NO_x$ gases may also be difficult to detect in a reliable manner.

One other problem with the known solutions is that in order to provide a fail safe detector, the power use and number of moveable parts should be kept at a minimum and thus complex systems e.g. incorporating pumps, as described in U.S. Pat. No. 5,886,247, should be avoided. Another complex system for monitoring gas is described in US2007/285222 where detector heads, e.g. for detecting hydrogen sulphide is positioned at different levels in a column, thus separating the gases to be detected. Another solution related to the use in oil and gas production is discussed in U.S. Pat. No. 7,705,988, where it is stated that the reliability of optical hydrogen sulphide detection is low and thus the detection is linked to the amount of methane and the known ratio of hydrogen sulphide in the flow.

There are a number of different measurement principles that may be used for hydrogen sulphide/$H_2S$ detection, like catalytic, electrochemical and MOS, but typically these sensors will not be able to detect functional failure. This means that the sensors may stop working, but the users get no information about this.

Thus there is a need for a simple optical gas detector providing reliable results for noxious gases, and where the detector is able to verify its own functional status. This is obtained as described in the accompanying claims.

The present invention thus provides a solution where the monitored gas moves through a catalyst membrane converting it to an easily detectable gas, e.g. converting $H_2S$ to $SO_2$, and where the operation of the sensor is verified by detecting possible clogging which results in reduction or complete stop in the reduction in the circulation in the unit and through the membrane.

The invention will be described more in detail with reference to the accompanying drawings, illustrating the invention by way of example.

FIG. 3a,b illustrates schematically the detection cells according to the invention.

FIG. 4a,4b illustrates the membranes of FIGS. 3a,3b as seen from the front.

Figure 5:
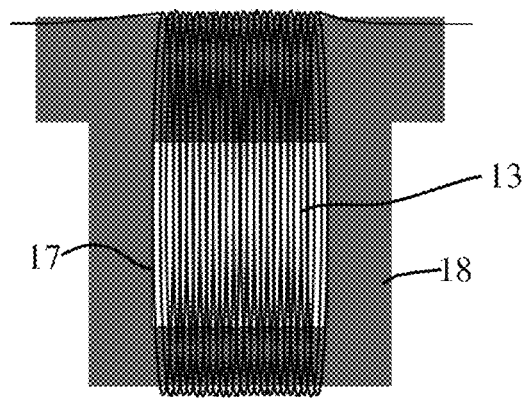

FIG. 5 illustrates an embodiment where the catalyst constituting the membrane is a wound string covering the opening.

Figure 6:
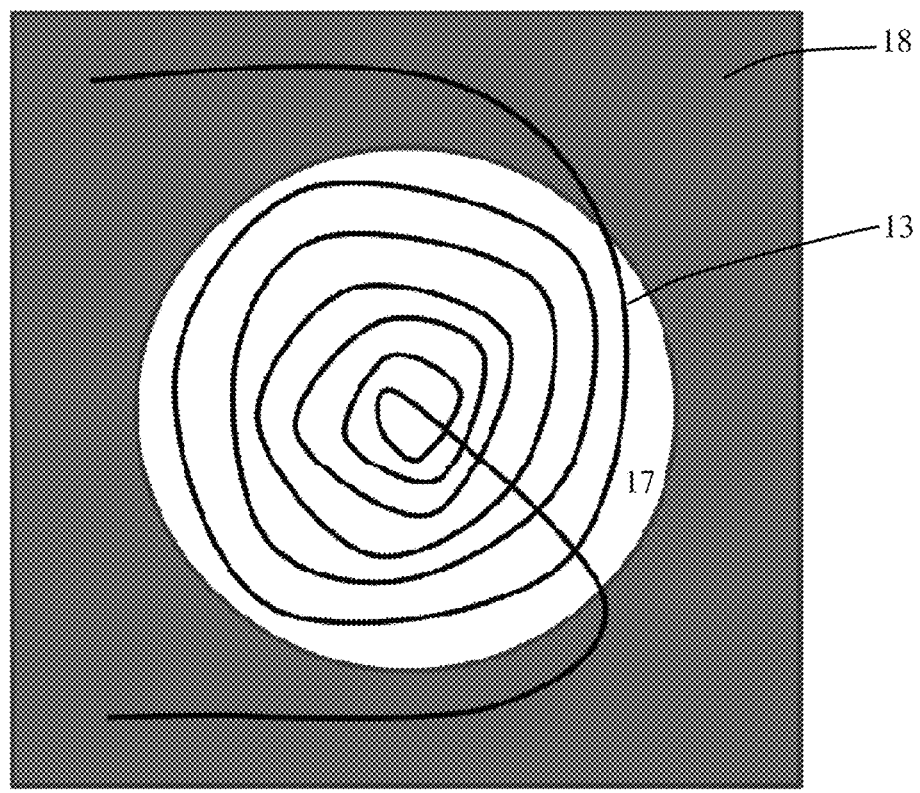

FIG. 6,7 illustrates alternative layouts of a catalyst string constituting a membrane.

Figure 8:
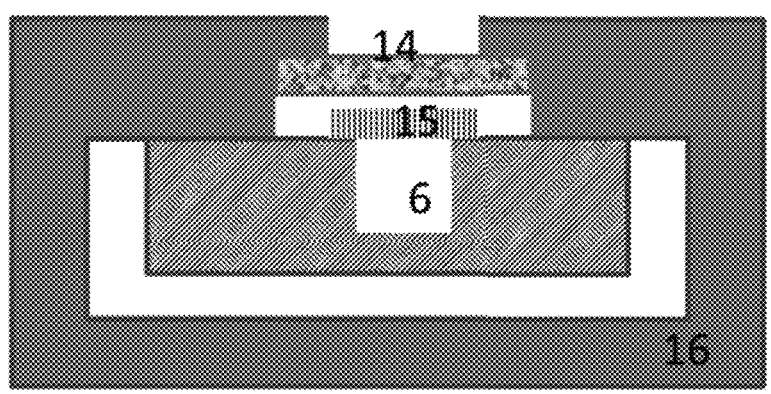

FIG. 8 illustrates the system according to the preferred embodiment of the invention with an explosion proof encapsulation. This kind of encapsulation would typically be consisting of a flame arrestor such as a sinter filter allowing the gas to enter, but not explosion or a flame to propagate through; and a solid encapsulation around the whole system.

Figure 1:
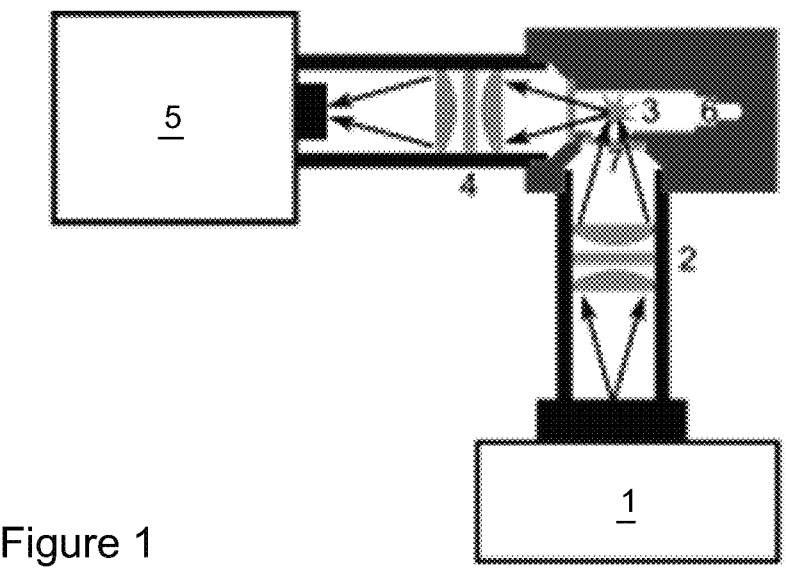
FIG. 1 illustrates the optical system including the gas detection cell.

FIG. 1 illustrates a measuring system related to fluorescence measurements where a light source 1 emits light through a lens system 2 (for focusing light inside an optical cell 6 and optical filter), the light being focused 3 in a cell 6 preferably having an inner surface being coated so as to avoid light being reflected therein from the light source 1 into the optical sensor 5. In the focus point 3 a fluorescence reaction is obtained (gas is absorbed and light is emitted in a different wavelength), the light therefrom propagating through a second lens system 4 to the optical sensor 5 being capable of detecting the wavelength and intensity of the received light.

The cell 6 is usually closed except for the opening with the catalyst membrane leading the gas into the cell. The cell in the illustrated example also being provided with windows 7 for letting the light into and out of the cell, the windows being angled to reduce the reflections from the light source inside the cell.

Other measuring systems may be used, e.g. for measuring the spectrum of the light transmitted directly through the cell, the important aspect being that the system includes a cell confining a fluid, especially a gas, to be measured.

Figure 2:
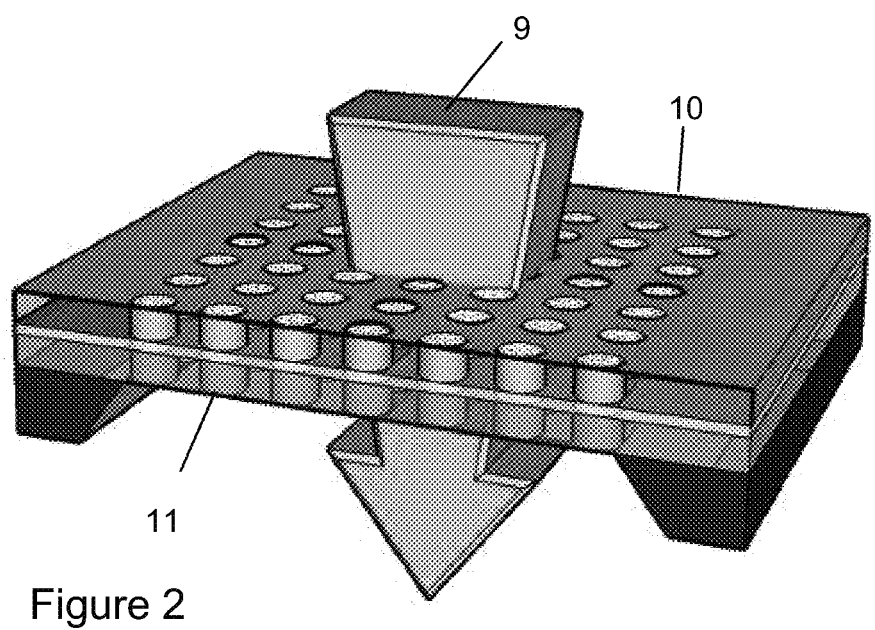
FIG. 2 illustrates the catalyzing membrane according to the preferred embodiment of the invention.

According to the present invention the enclosed volume constituting the cell 6 is provided with at least one wall or wall part as illustrated in FIG. 2, being provided with openings for letting a target gas move through it. The nature of the openings may differ, but are chosen so as to allow diffusion of the target gas.

Figure 7:
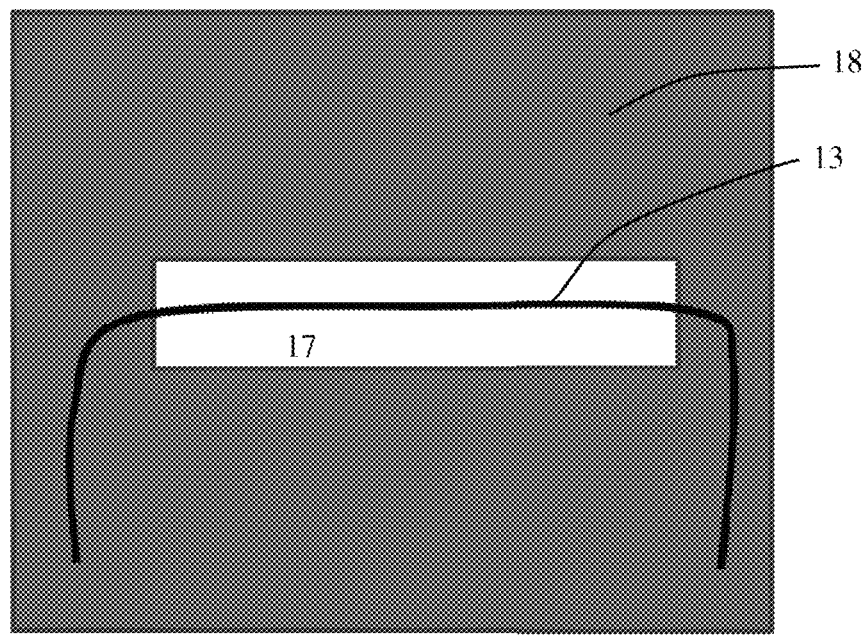

In FIG. 2 the wall is a silicon membrane 10 being perforated 11 with openings through which the gas 9 may move. In general the perforated wall 11 in the cell as illustrated in FIG. 3a, while FIG. 3b illustrates the use of a net 12 or other material to provide the openings. FIGS. 4a and 4b illustrate the perforated wall 11 or net 12 in FIGS. 3a and 3b, respectively, while FIGS. 5, 6 and 7 illustrate the use of one or several crossings of a wire or catalyst string 13 over an opening 17 in the wall 18, thus illustrating that the area has to be sufficiently open to allow the gas to move through.

According to the present invention the membrane 10,11, 12,13 is provided with a catalyst so as to provide a chemical reaction. The catalyst usually being heated for providing the reaction. In the preferred embodiment of the invention for detecting $H_2S$ the catalyst is chosen so as to convert the gas into $SO_2$, which is easy to detect in a suitable optical system.

As stated above the catalyst in the system may be of different types depending on the gas conversion. In the case of $H_2S$ the catalyst may be made from FeCrAl alloys (i.e. Kanthal) heated to a suitable temperature, e.g. between 300 and 500 degrees Celsius to obtain close to 100% conversion. At lower temperatures, i.e. 200 degrees Celsius, less than 100% of the gas is converted, but the sensor principle still works. In one embodiment, the heating element is a woven mesh of FeCrAl alloy, and the heating is performed by connecting the membrane to an electric power source, and turn the power to obtain the required temperature. The FeCrAl alloy wire thickness may be in the range of 0.05 mm to 0.2 mm. FeCrAl alloy is very well suited for this kind of combined heating, as the surface for certain kinds of FeCrAl alloy may withstand temperatures of above 1500 degrees Celsius, allowing several years of lifetime operated below 500 degrees Celsius.

The FeCrAl alloy woven mesh may be coated with $Fe_2O_3$ or $Cr_2O_3$ to improve conversion of $H_2S$ to $SO_2$. Other types of coating like CuO or $Cu_2O$, also work, and at higher temperatures a surface of $Al_2O_3$ can be used. Oxides and sulfides of Co, Mo, Ni, W, V, Al and Mn are also possible candidates as catalytic converters. For other types of gases, the FeCrAl alloy woven mesh may be coated with different types of coatings.

In another embodiment, the FeCrAl alloy is not a woven mesh, but a wire wrapped around a frame as illustrated in FIG. 5. Typically, a FeCrAl alloy wire with diameter around 0.1 mm and period of 0.15 mm may be used. The advantage with this approach over the woven mesh approach, is that the resistance of the heater increases, and this may be advantageous in applications where the available current is limited.

Preferably the membrane is pretreated to not absorb the $H_2S$ during the measurements. Further, the membrane goes through a burn in of the surface to obtain stable operation.

The structure illustrated in FIG. 2 is a silicon membrane being provided with a heating layer and silicon dioxide or silicon nitride surfaces. The silicon membrane is provided with a number of holes to let the gas through at the same time as the gas is heated, and the gas reacts with the catalyst. The catalyst may be coated onto the silicon dioxide or silicon nitride surface, or the surface may be provided with a layer of $Al_2O_3$ (by i.e. Atomic Layer deposition), and then coated with the above mentioned catalysts. The heater may be made of other types of semiconductors or ceramic compositions as well.

The cross section of the position where the heated catalyst is placed may typically be in the range 1 to 100 $mm^2$, depending on the response time required by the sensor. The response time is given by the volume of the optical sensor chamber cell 6 and the amount of gas able to diffuse through the converter. A small volume will typically give a fast response time, since less gas needs to be converted, and a small volume will also require less power for the same reason. A reasonable response time can be obtained for volumes up to 4 cm3. Typically, the optical sensor chamber cell 6 has a volume of less than $(1 \text{ cm})^3$ and more typically $(5 \text{ mm})^3$.

The fill factor (i.e. wire to hole ratio) of the heater substrate (wire, membrane or woven mesh) is typically in the range of 50%, allowing diffusion and conversion of the gas in less than a few seconds. With lower fill factor, the time required for the conversion, will increase, but the sensor principle still works, only with slower response.

Calibration of the offset can be performed by turning off the temperature of the heated catalyzer for a period of time to cool down the converter to a temperature where conversion don't take place (this takes typically between 0.5 to 100 seconds), and measure the signal response. This signal response cannot be from the targeted gas, since the converter is turned off, and this offset signal can be subtracted from the baseline to obtain good calibration of the zero gas level. This zero level calibration can be done by software from time to time, typically once a week or once a month.

In the case of a $H_2S$ sensor, the presence of $SO_2$ may give an error in the calibration of the zero level. This may be improved. E. Xue, K. Seshan, J. R. H. Ross: "Roles of supports, Pt loading and Pt dispersion in the oxidation of NO to NO2 and of $SO_2$ to SO3", published in Applied Catalysis B: Environmental 11 (1996) 65-79, describes how a platinum (Pt) catalyst heated to about 300 degrees C. can be used to convert $SO_2$ to $SO_3$. By converting the gas from $SO_2$ to $SO_3$, we can remove $SO_2$ from the measurement, and thereby perform a zero calibration of the instrument online. This will be done by heating the platinum catalyst to around 350 degrees C. at the same time as the $H_2S$ to $SO_2$ catalyst is turned off. When steady state is obtained, a measurement of the remaining signal amplitude will be performed, and this amplitude, also called an offset, will be subtracted from the following measurements to obtain good calibration of the zero gas level.

For a sensor used in hazardous and explosive environments, the surface temperature must be kept below a certain limit. Typically, a sintered filter 14 is used to isolate the high temperature catalyst 15 from the surrounding environment to avoid explosions or ignition, and is illustrated in FIG. 8. The function of the sintered filter is also to prevent a spark, flame or explosion to propagate from inside the detector enclosure 16 to the outside. A possible function failure may be that the sintered filter 14 is partly clogged and thereby limits the gas diffusion through the sintered filter. This will give an increase in response time for the sensor, and in the worst case, where the sintered filter is totally clogged, the sensor will give no response at all. It is therefore important to identify such clogging, and output a signal indicating the failure.

In general, a functional failure where a sinter filter is clogged can be identified by the change in the transfer function or impulse response of the sinter filter. This transfer function may be measured by imposing a step and measuring the response. A step response in the form of an increased pressure may be imposed at a given time, and the transfer function or the step response of the sinter filter can be measured with a pressure sensor. Typically, the time response will increase when the clogging of the filter increase. The step response can be made by several methods, i.e. a pumping mechanism or a loudspeaker changing the volume inside the sinter filter, a rapid change in temperature giving a rise in pressure in the volume inside the sinter filter, or letting in or out some gas changing the pressure, i.e. from a chamber with a different temperature. Instead of measuring the impulse response of the sintered filter, parts of the transfer function can be sampled by measuring the frequency response on one or several frequencies. The sintered filter will work as low pass acoustic filter, letting though slow variations in pressure (sound) and filtering away higher frequencies. In example, we can modulate a small load speaker with a frequency close to the frequency f0 given by the time constant of the sintered filter. We measure the signal response inside the measurement cell, where the sintered filter is the only way to the outside. The change in amplitude or/and phase can be used to estimate the time constant of the system, and thereby verify that the sintered filter is letting the gas in. Several frequencies may be used to improve the accuracy of this method.

The functional failure of the sintered filter may also be measured by another method. A working sintered filter is letting gas through, and the outside gas is much colder than the gas inside the cell, due to the heating of the catalyst. This means that the gas temperature close to the sintered filter will be lower when the sintered filter transmits gas, while the temperature will increase when the sintered filter is clogged. The accuracy of the method can be increased by measuring the gas temperature on several positions, including the outside temperature. Further, the gas temperature inside the sensor may be modulated or stepped, to measure the transfer function or impulse response as described above.

As an example, NOx can be converted to $N_2O$ with platinum (Pt), palladium (Pd), rhodium (Rh) catalysts, or combinations of these, as described in "Emissions of nitrous oxide and methane from alternative fuels for motor vehicles and electricity-generating plants in the U.S.", ucd-its-rr-03-17f, December 2003, T. Lipman and M. Delucchi. When NOx is converted to $N_2O$, $N_2O$ can easily be detected by optical methods like infrared spectroscopy.

It takes longer time and more energy to convert a large volume of gas than to convert a small volume of gas. For fast response sensors and low energy consumption, the volume of converted gas must be as small as possible. This favors to types of optical detection: a) Fluorescence detection, and b) Photo acoustic detection, which both works fine on very small gas volumes.

In some cases, where a pulsed source like a Xenon flash lamp is used, the total number of pulses available through the lamps lifetime is limited. In other cases, the available power is limited, and we want to save energy by using as little power as possible. To avoid false alarms, the following procedure has been invented. When a pulsed source is used to detect the gas, the pulsed source is typically operated at a given frequency, and the signal processing unit estimates a gas level at or above a predetermined alarm limit, the sensor performs a verification of the estimated gas level by increasing the frequency of the pulsed source by a predetermined factor (i.e. 30 times), and average these results over a limited period of time (i.e. 0.5 seconds) which typically is much shorter than the sensor response time. The averaged result (or a modified version of this incorporating previous measurements) is then given as the sensor output, to avoid false alarms.

Thus to summarize the present invention relates to a gas detector cell for optical detection of a predetermined gas, the cell being provided with optical means for investigating a gas sample present in the cell. The cell is constituted by a volume enclosed in a container, at least part of the container wall being constituted by a membrane, where the membrane is provided with openings allowing diffusion of gas therethrough. In the membrane openings a catalyst is positioned for converting the gas diffusing therethrough to said predetermined gas. The thickness of the membrane is not important, thus the term in this case may include a wide range, but the openings are chosen so as to allow a diffusion of gas through them.

The predetermined gas is preferably $H_2S$ and the gas sample is $SO_2$, in which case the catalyst is adapted to convert $H_2S$ passing through the openings in said membrane to $SO_2$. The catalyst may then be made from a mesh, a membrane with holes, a wire or another construction sufficiently open to allow gas passing though the openings. The catalyst in this case preferably being made from a FeCrAl alloy.

One alternative to this is shown in FIG. 2 where the membrane is made from a silicon membrane being provided with openings and being treated with $Fe_2O_3$ or $Cr_2O_3$. Another alternative is a silicon membrane being provided with openings and being treated with an oxide of Cu, Co, Mo, Ni, W, V, Al or Mn.

The predetermined gas may also be NOx, and the catalyst is then adapted to convert NOx passing through the openings in said membrane to N2O.

The volume of the gas sample present in the cell may vary with the method for measuring the content, and in the case of $H_2S$ may be less than 1 cm$^3$, possibly is less than (5 mm)$^3$.

The optical detection means may be based on fluorescent detection, being a well known method discussed above and not to be described in any further detail here. Alternatively the optical means is constituted by a photo acoustic detection means, which is also well known and discussed above. The choice of measuring means will depend on the gas to be detected as well as other, practical considerations.

Both in fluorescence and photoacoustic detection a pulsed source may be used to detect the gas. The pulsed source is operated at a given frequency and a signal processing unit estimates a gas level at or above a predetermined alarm limit depending on the gas type and risk considerations. According to one embodiment the sensor is adapted to provide a verification of the estimated gas level by increasing the frequency of the pulsed source by a predetermined factor (i.e. 30 times), and average these results over a limited period of time (i.e. 0.5 seconds). The averaged result (or a modified version of this, incorporating previous measurements) is then given as the sensor output in order to avoid false alarms.

Calibration of a gas sensor cell may be performed by turning the catalyst on and off, for example by controlling the temperature of the catalyst. The calibration may then be performed by turning off the temperature of the heated catalyzer for a period of time to cool down the converter to a temperature where conversion does not take place, e.g. between 0.5 to 100 seconds, and measure the signal response as an offset value. The measurements may then be compensating for the offset by subtracting the measurements without conversion from the measurements with an active catalyst.

An alternative calibration method may be performed by providing a second catalyst or converter adapted to remove or adsorb the predetermined gas in the cell, the second converter being activated for a limited time, e.g. 5 seconds and providing an offset calibration during the activation time of said second catalyst.

As the catalyst may be heated during operation it must in some operations, e.g. when used in hazardous and explosive environments, be positioned inside an enclosure as illustrated in FIG. 8. Access to the gas outside this gas cell unit is then through a filter making this sensor safe for use explosive environments, i.e. a sintered filter. A sintered filter is, however prone to clogging which reduce the sensitivity of the gas cell or even not be able to detect the gas at all. Thus in these cases the gas cell unit has to be provided with means for detecting the clogging, and provide a signal to an operator or similar indicating a possible system failure.

The clogging may be detected using detection means adapted to analyze the transfer function or impulse response of the sinter function by applying a pressure variation or acoustic signal inside said housing, and comparing the resulting pressure variations in the housing with reference measurements based on a clean, open sintered filter. This may alternatively be performed by applying a temperature variation and considering the response in the temperature inside the housing. If the temperature outside the housing is known it is also possible to detect the clogging by simply monitoring the inside temperature and compare it with the outside temperature, as the clogging will reduce the circulation and thus may result in an increasing temperature inside the housing.

The invention claimed is:

1. A gas detector cell unit comprising:
   a gas cell having:
      a diffusive membrane, the diffusive membrane having at least one opening;

an outer housing having a passage for a first incoming gas outside the outer housing to pass therethrough;

a protecting filter in fluid communication with the passage, the gas detector cell unit detecting a reduction in circulation through the protecting filter based at least in part on a change in a pressure transfer function of the protecting filter over a predefined time; and a catalyst being located proximate the at least one opening of the diffusive membrane, the catalyst converting the first incoming gas to a predetermined second gas, the gas detector cell unit detecting the predetermined second gas.

2. The gas detector cell unit according to claim 1, wherein the gas detector cell unit generates a signal for indicating system failure.

3. The gas detector cell unit according to claim 1, wherein the pressure transfer function of the protecting filter is in response to a pressure variation inside the housing.

4. The gas detector cell unit according to claim 1, wherein the filter is a sintered filter.

5. The gas detector cell unit according to claim 1, wherein the pressure transfer function of the protecting filter is based at least in part on a predefined step pressure increase imposed on the gas detector cell unit.

6. The gas detector cell unit according to claim 1, wherein the detecting of the reduction in circulation through the protecting filter is based at least in part on a time constant of the gas detector cell.

7. The gas detector cell unit according to claim 1, wherein the detecting of the reduction in circulation through the protecting filter based at least in part on a change in a pressure transfer function includes sampling parts of the pressure transfer function by measuring the frequency response at at least one frequency.

* * * * *